(12) United States Patent
Mori et al.

(10) Patent No.: US 9,198,837 B2
(45) Date of Patent: Dec. 1, 2015

(54) DENTAL GYPSUM-BONDED INVESTMENT MATERIAL POWDER

(71) Applicant: GC CORPORATION, Bunkyo-ku (JP)

(72) Inventors: Daizaburo Mori, Saitama (JP); Emiko Fukushima, Koshigaya (JP); Haruhiko Horiuchi, Chiba (JP)

(73) Assignee: GC CORPORATION, Bunkyo-ku (JP)

( * ) Notice: Subject to any disclaimer, the term of this patent is extended or adjusted under 35 U.S.C. 154(b) by 149 days.

(21) Appl. No.: 14/037,698

(22) Filed: Sep. 26, 2013

(65) Prior Publication Data
US 2014/0083326 A1    Mar. 27, 2014

(30) Foreign Application Priority Data
Sep. 26, 2012   (JP) ................ 2012-213006

(51) Int. Cl.
| | | |
|---|---|---|
| *A61K 6/00* | (2006.01) | |
| *C04B 11/00* | (2006.01) | |
| *A61K 6/10* | (2006.01) | |
| *A61K 6/06* | (2006.01) | |
| *C04B 103/40* | (2006.01) | |
| *C04B 103/50* | (2006.01) | |

(52) U.S. Cl.
CPC .............. *A61K 6/0088* (2013.01); *A61K 6/0625* (2013.01); *A61K 6/10* (2013.01); *C04B 11/00* (2013.01); *C04B 2103/402* (2013.01); *C04B 2103/50* (2013.01)

(58) Field of Classification Search
CPC ...... A61K 6/10; C04B 11/00; C04B 2103/50; C04B 2103/402
See application file for complete search history.

(56) References Cited

U.S. PATENT DOCUMENTS
4,911,759 A    3/1990    Ohi et al.

FOREIGN PATENT DOCUMENTS

| GB | 2 187 729 A |   | 9/1987 |
|---|---|---|---|
| JP | 05-155731 A |   | 6/1993 |
| JP | 05-319951 A |   | 12/1993 |
| JP | 06-133990 A |   | 5/1994 |
| JP | 06-178926 A |   | 6/1994 |
| JP | 2013-159602 | * | 8/2013 |

OTHER PUBLICATIONS

Derwent abstract for CN 1010804442A, Aug. 18, 2010.*
Extended European Search Report issued Jan. 14, 2014 in Patent Application No. 13004674.1.

* cited by examiner

*Primary Examiner* — Carol M Koslow
(74) *Attorney, Agent, or Firm* — Oblon, McClelland, Maier & Neustadt, L.L.P.

(57) ABSTRACT

The invention provides a dental gypsum-bonded investment material powder which can inhibit air bubbles from being generated in a mixed material, only by being mixed with water without using any special device or tool, and is easily mixed with the water. A specific siloxane is blended at a specific amount in relation to the dental gypsum-bonded investment material powder which includes an anionic surfactant and is excellent in a mold releasing action. In other words, the dental gypsum-bonded investment material powder is structured such as to have 0.001 to 0.2 weight % anionic surfactant, and 0.00001 to 0.0005 weight % cyclic siloxane having 3 to 10 $SiO(CH_3)_2$ units.

8 Claims, No Drawings

DENTAL GYPSUM-BONDED INVESTMENT MATERIAL POWDER

BACKGROUND OF THE INVENTION

1. Field of the Invention

The present invention relates to a dental gypsum-bonded investment material powder which can manufacture a dental metal restoration material having no defect while preventing air bubbles from being mixed into a paste corresponding to a mixed material in the case of being mixed with water.

2. Description of the Conventional Art

The dental metal restoration material is manufactured by procedures of forming a shape of a restoration material by a wax material on the basis of a precise casting technique according to a lost-wax process, attaching a sprue line (a molten metal injection port) thereto, embedding it with a dental embedding material, extracting the sprue line after the dental embedding material is set, and injecting a molten metal into a cavity which is formed by burning and removing the wax. Particularly, the dental metal restoration material is demanded a higher dimensional precision since the dental metal restoration material is installed to an oral cavity so as to be used for the purpose of restoring a defect part of the tooth. In order to obtain the dental metal restoration material which is excellent in precision, it is necessary to compensate a casting shrinkage of the metal, by utilizing an expansion of the dental embedding material when the dental embedding material is set and heated.

The dental embedding material generally has two kinds of material including a gypsum-bonded investment material obtained by mixing a fire resisting material such as quartz and/or cristobalite with an α hemihydrate gypsum as a bonding material, and a phosphate-bonded investment material obtained by mixing the fire resisting material such as the quarts and/or the cristobalite with an ammonium dihydrogenphosphate and a magnesium oxide as a bonding material, and having a high heat resistance. In the case of a dental casting alloy of noble metal for inlaying, crowning and bridging which is defined by JIS standard as a liquid phase point is equal to or lower than 1000 to 1100° C. [dental casting silver alloy (JIS T 6108), dental casting gold, silver and palladium alloy (JIS T 6106), dental casting gold alloy (JIS T 6116)], the gypsum-bonded investment material is used, and in the case of a dental casting porcelain baking noble metal alloy which has a high liquid phase point (equal to or higher than 1100° C.) so that the alloy can stand against a baking work (about 1000° C.) of the porcelain after casting, the phosphate-bonded investment material is used.

An importance for the precise dental restoration material exists in a matter that the air bubbles are not mixed into the paste corresponding to the mixed material at a time when the dental gypsum-bonded investment material powder and the water are mixed. In the dental gypsum-bonded investment material, since the air is included generally in the investment material powder, the air bubbles tend to enter into the dental gypsum-. If the air bubbles are mixed into the paste, a concave shape is formed by casting into the dental metal restoration material. Therefore, a repairing operation such as a trimming operation is necessary after the casting.

In order to reduce the air bubbles which are generated at the mixing time, there is a defoaming method of a dental material mixed material which agitates the mixed material by using a defoaming device in which a handle portion is attached to a defoaming member having a curved surface (refer, for example, to patent document 1). However, this method needs employment of a dedicated device.

Consequently, there has been developed a dental gypsum-bonded investment material powder which generates less air bubbles at a time of being mixed. For example, there is a mixing method of adding an emulsion structured such that an anionic surfactant is dispersed as an emulsifying agent into the water to a silicone oil, which is carried out in a dental gypsum field (refer, for example, to patent documents 2 and 3). However, in these methods, it is necessary to prepare the dedicated emulsifying agent in addition to the powder and the water, a handling has been complicated. Further, there has been a defect that it is necessary to prepare the dedicated mixing solution even if the emulsifying agent is mixed with the water. Further, since the anionic surfactant is mainly used for a mold release agent in relation to the wax, there has been a problem that the powder is hydrophobic and it is hard to mix with the water.

Patent Document 1: Japanese Unexamined Patent Publication No. 5-155731

Patent Document 2: Japanese Unexamined Patent Publication No. 6-133990

Patent Document 3: Japanese Unexamined Patent Publication No. 6-178926

SUMMARY OF THE INVENTION

Problem to be Solved by the Invention

An object of the present invention is to provide a dental gypsum-bonded investment material powder which can inhibit air bubbles from being generated in a mixed material, only by being mixed with water without using any special device or tool, and is easily mixed with the water.

Means for Solving the Problem

The inventors of the present invention have devoted themselves to make a study for solving the problem mentioned above. As a result, the inventors have found that it is possible to improve compatibility with water on the basis of an effect of a specific siloxane, in addition to an effect of improving compatibility with wax in the anionic surfactant, by blending the specific siloxane at a specific amount in relation to the dental gypsum-bonded investment material powder which includes the anionic surfactant and is excellent in a mold releasing action in relation to the wax, and have completed the present invention.

In other words, the dental gypsum-bonded investment material powder according to the present invention is a dental gypsum-bonded investment material powder comprising 0.001 to 0.2 weight % anionic surfactant, and 0.00001 to 0.0005 weight % cyclic siloxane having 3 to 10 $SiO(CH_3)_2$ units.

Effect of the Invention

The dental gypsum-bonded investment material powder according to the present invention is the dental gypsum-bonded investment material powder which can inhibit air bubbles from being generated in the mixed material without using any special emulsifying agent or any mixing solution, and can be easily mixed with the water.

DETAILED DESCRIPTION OF PREFERRED EMBODIMENT

A description will be in detail given below of an embodiment according to the present invention. A dental gypsum-bonded investment material powder according to the present invention includes 0.001 to 0.2 weight % anionic surfactant. The anionic surfactant is blended for improving compatibility with a wax model. As the anionic surfactant, a sodium dodecyl benzene sulfonate can be used as an alkyl benzene sulfonate. Further, as an alkyl sulfate, conventionally used materials such as a sodium lauryl sulfate, a potassium lauryl sulfate, a sodium myristyl sulfate, a sodium cetyl sulfate, and a sodium stearate can be used. If a blending amount of the anionic surfactant into the dental gypsum-bonded investment material powder is less than 0.001 weight %, the compatibility with the wax is lowered, and if the blending amount goes beyond 0.2 weight %, the mixing property with the water is lowered.

The dental gypsum-bonded investment material powder according to the present invention is blended with the specific siloxane in a range that the effect of the anionic surfactant is not neutralized. The specific siloxane is a cyclic siloxane having 3 to 10 $SiO(CH_3)_2$ units, and is included at 0.00001 to 0.0005 weight % in the dental gypsum-bonded investment material powder. By blending the specific cyclic siloxane, it is possible to inhibit the air bubbles from being generated at a time of mixing the dental gypsum-bonded investment material powder with the water, and it is possible to improve the mixing property. Further, since the effect can be obtained by a small blending amount, various performance of the set material are not adversely affected. A desired effect can not be obtained if the amount of the cyclic siloxane having 3 to 10 $SiO(CH_3)_2$ units is smaller than 0.00001 weight %, and the mixing property with the water is deteriorated as the dental gypsum-bonded investment material powder if the amount goes beyond 0.0005 weight %.

The cyclic siloxane having 3 to 10 $SiO(CH_3)_2$ units has three to ten $SiO(CH_3)_2$ units (hereinafter, refer to as D unit). For example, a case that D is 3 means a hexamethyl cyclo trisiloxane, a case that D is 4 means an octamethyl cyclo tetrasiloxane, and a case that D is 5 means a decamethyl cyclo pentasiloxane. A preferable number of the $SiO(CH_3)_2$ unit is between 3 and 5, and the octamethyl cyclo tetrasiloxane in which D is 4 is most preferable particularly in the light of easiness of blending and height of effect. The cyclic siloxane having different number of D can be mixed and used.

In the dental gypsum-bonded investment material powder, an operationality and a physical property are set in correspondence to an intended purpose, however, since the used hemihydrate gypsum itself is quickly set, a curing retardant is normally added. As the curing retardant, it is possible to use the known curing retardant, for example, salts such as a citrate salt, a borate salt, a carboxylate salt and an acetate salt, and a water-soluble polymer such as a starch, a gum acacia, a carboxymethyl cellulose, and a gelatin. The curing retardant is normally included at 0.00001 to 0.2 weight part in relation to the hemihydrate gypsum powder 100 weight part in the dental gypsum-bonded investment material powder.

In the case that it is necessary to subtly adjust a curing time, a curing accelerator may be further used. As the curing accelerator, it is possible to use the known curing accelerator, for example, inorganic salts such as a sodium chloride and a potassium sulfate, and a gypsum dihydrate superfine powder. In the case of being blended, the curing accelerator is normally included at 0.001 to 2 weight part in relation to the hemihydrate gypsum powder 100 weight part in the dental gypsum-bonded investment material powder.

A setting expansion inhibitor such as a potassium tartrate may be blended in the dental gypsum-bonded investment material powder according to the present invention. It is preferable that the setting expansion inhibitor is included at 0.01 to 1 weight part in relation to the hemihydrate gypsum-bonded investment material powder 100 weight part.

Since the dental gypsum-bonded investment material powder according to the present invention is obtained by adding and mixing the anionic surfactant and the specific cyclic siloxane to the power side of the dental gypsum-bonded investment material, it is possible to use the conventional dental gypsum-bonded investment material powder having the hemihydrate gypsum as a main component. The hemihydrate gypsum includes an α hemihydrate gypsum, a β hemihydrate gypsum, and a mixture of the α hemihydrate gypsum and the β hemihydrate gypsum. Further, the hemihydrate gypsum keeps the same powder state as the conventional dental gypsum-bonded investment material powder, and is used by adding an appropriate amount of water to the powder, for example, adding 18 to 28 weight part of water to 100 weight part of powder so as to form a paste state, and molding and curing into an optional shape. Therefore, it is not necessary to any special emulsifying agent or any dedicated mixing solution.

The dental gypsum-bonded investment material powder according to the present invention may additionally include any known coloring agent or weight saving material as occasion demands.

There is below listed up an example of the dental gypsum-bonded investment material powder according to the present invention, however, the present invention is not limited to the example.

EXAMPLES

<Raw Powder A Mixed with Cyclic Siloxane Blended Silicon Oil>

A diluted powder of silicon oil 1 weight % (cyclic siloxane 0.05 weight %) is prepared by mixing 1 g of silicon oil (polydimethylsiloxane) including 4 weight % of hexamethyl cyclo trisiloxane, and 1 weight % of octamethyl cyclo tetrasiloxane with 99 g of α hemihydrate gypsum powder and agitating for one hour. The powder is set as a raw powder A. The raw powder A is mixed with the dental gypsum-bonded investment material powder described in the example according to a rate shown in Table 1.

<Raw Powder B Mixed with Cyclic Siloxane Blended Silicon Oil>

A diluted powder of silicon oil 1 weight % (cyclic siloxane 0.1 weight %) is prepared by mixing 1 g of silicon oil (polydimethylsiloxane) including 10 weight % of octamethyl cyclo tetrasiloxane with 99 g of α hemihydrate gypsum powder according to the method mentioned above. The powder is set as a raw powder B. The raw powder B is mixed with the dental gypsum-bonded investment material powder described in the example and a comparative example according to a rate shown in Table 1.

<Raw Powder C Including No Cyclic Siloxane Blended Silicon Oil and Mixed Only with Silicon Oil (for Comparative Example)>

A diluted powder of silicon oil 1 weight % (cyclic siloxane 0 weight %) is prepared by mixing 1g of silicon oil (polydimethylsiloxane) with 99 g of dental gypsum powder described in Table 1 according to the method mentioned above. The powder is set as a raw powder C. The raw powder C is mixed with the dental gypsum-bonded investment material powder described in the comparative example according to a rate shown in Table 1.

A final blending and results of tests of each of the examples and the comparative examples are collectively shown in Table 1.

<Evaluation of Defoaming Property>

100 g of the dental gypsum-bonded investment material powder which is prepared in each of the embodiments and the comparative examples and 23 g of water are fed in a rubber bowl and are mixed by a spatula, and the mixed paste is poured into a mold having a diameter 25 mm and a height 50 mm so as to be left for 30 minutes. The set material is cut into halves, and a degree of air bubbles recognized on a cut surface is evaluated by a visual observation. A mark X is given to a case that the degree is about the same as the set material using the conventional gypsum-bonded investment material powder (comparative example 2), and a mark E is given to a case that the air bubbles are apparently reduced. Results are collectively shown in Table 1.

<Evaluation of Mixing Property at the Mixing Time>

100 g of the dental gypsum-bonded investment material powder which is prepared in each of the embodiments and the comparative examples and 23 g of water are fed in the rubber bowl and are mixed by the spatula, and a mixing property at the mixing time is evaluated by feeling in comparison with the conventional gypsum-bonded investment material powder (comparative example 2). Results are collectively shown in Table 1.

<Evaluation of Wetting Property to Wax>

100 g of the dental gypsum-bonded investment material powder which is prepared in each of the embodiments and the comparative examples and 23 g of water are fed in the rubber bowl and are mixed by the spatula, the mixed paste is flowed on a wax plate having vertical and horizontal lengths 50 mm and a height 4 mm, and an expanding distance is checked. A mark E is given to a case that the expansion is equal to or more than the expansion of the set material using the conventional gypsum-bonded investment material powder (comparative example 2), and a mark X is given to a case that the expansion is smaller.

<Easiness of Mixing with Water (Difficulty in Scattering of Powder>

100 g of the dental gypsum-bonded investment material powder which is prepared in each of the embodiments and the comparative examples and 23 g of water are fed in the rubber bowl and are mixed by the spatula, and a scattering degree of the powder is checked by feeling. A mark E is given to a case that the powder scattering is about the same as the conventional gypsum-bonded investment material powder (comparative example 2), and a mark X is given to a case that the powder is easy to scatter and is hard to be mixed with the water.

<Test of Property>

In the dental gypsum-bonded investment material powders according to the examples and the comparative examples, the physical natures (the setting time and the flow property) are measured according to method defined in JIS T 6601 "Dental Casting Gypsum-bonded investment Material". Results are collectively shown in Table 1.

TABLE 1

| | | example 1 | | example 2 | | example 3 | | example 4 | |
|---|---|---|---|---|---|---|---|---|---|
| | | | | | | | | Unit of blending weight % | |
| α hemihydrate gypsum | | 34.4 | | 33.7 | | 33.7 | | 34.68 | |
| cristobalite | | 65 | | 65 | | 65 | | 65 | |
| raw material A | polydimethylsiloxane | 0.1 | 0.00095 | 0.3 | 0.00285 | | | | |
| | *octamethyl cyclo tetrasiloxane | | 0.00001 | | 0.00003 | | | | |
| | *hexamethyl cyclo trisiloxane | | 0.00004 | | 0.00012 | | | | |
| | α hemihydrate | | 0.099 | | 0.297 | | | | |
| raw material B | polydimethylsiloxane | | | | | 0.3 | 0.0027 | 0.3 | 0.0027 |
| | *octamethyl cyclo tetrasiloxane | | | | | | 0.0003 | | 0.0003 |
| | α hemihydrate | | | | | | 0.297 | | 0.297 |
| raw material C | polydimethylsiloxane | | | | | | | | |
| | α hemihydrate | | | | | | | | |
| anionic surfactant | sodium dodecyl benzene sulfonate | 0.5 | 0.015 | 1 | 0.03 | 1 | 0.03 | 0.02 | 0.0006 |
| | sodium lauryl sulfate | | 0 | | 0 | | 0.97 | | 0 |
| | α hemihydrate | | 0.485 | | 0.97 | | 0 | | 0.0194 |
| defoaming property | | E | | E | | E | | E | |
| wetting property to wax | | E | | E | | E | | E | |
| easiness of mixing wih water (difficulty in scattering of powder) | | E | | E | | E | | E | |
| setting time (min sec) | | 11'30" | | 11'30" | | 11'30" | | 11'30" | |
| mixing property | | equal | | equal | | equal | | equal | |
| flow property (mm) | | 105 | | 106 | | 103 | | 105 | |

| | | comparative example 1 | | comparative example 2 | | comparative example 3 | | comparative example 4 | |
|---|---|---|---|---|---|---|---|---|---|
| | | | | | | | | Unit of blending weight % | |
| α hemihydrate gypsum | | 34.2 | | 35 | | 34.7 | | 34.68 | |
| cristobalite | | 65 | | 65 | | 65 | | 65 | |
| raw material A | polydimethylsiloxane | | | | | | | | |
| | *octamethyl cyclo tetrasiloxane | | | | | | | | |
| | *hexamethyl cyclo trisiloxane | | | | | | | | |
| | α hemihydrate | | | | | | | | |
| raw material B | polydimethylsiloxane | 0.8 | 0.0072 | | | | | | |
| | *octamethyl cyclo tetrasiloxane | | 0.0008 | | | | | | |
| | α hemihydrate | | 0.792 | | | | | | |

TABLE 1-continued

| | | | | | | |
|---|---|---|---|---|---|---|
| raw material C | polydimethylsiloxane | | | 0.3 | 0.003 | |
| | α hemihydrate | | | | 0.297 | |
| anionic surfactant | sodium dodecyl benzene sulfonate | | | | | 0.02 0.0006 |
| | sodium lauryl sulfate | | | | | 0 |
| | α hemihydrate | | | | | 0.0194 |
| defoaming property | | E | — | E | | x |
| wetting property to wax | | x | — | x | | x |
| easiness of mixing wih water (difficulty in scattering of powder) | | E | — | x | | x |
| setting time (min sec) | | 11'00" | 11'30" | 11'30" | | 11'30" |
| mixing property | | flow property is lowered 5 min after starting | — | flow property is extremely lowered just after starting | | equal |
| flow property (mm) | | 84 | 105 | 61 | | 105 |

*is cyclic siloxane having 3 to 10 SiO(CH$_3$)$_2$ units

What is claimed is:

1. A dental gypsum-bonded investment material powder, comprising:
   0.001 to 0.2 weight % anionic surfactant; and
   0.00001 to 0.0005 weight % cyclic siloxane comprising 3 to 10 SiO(CH$_3$)$_2$ units.

2. The dental gypsum-bonded investment material powder of claim 1, wherein the anionic surfactant comprises at least one of an alkyl benzene sulfonate and an alkyl sulfate.

3. The dental gypsum-bonded investment material powder of claim 1, wherein the anionic surfactant comprises an alkyl benzene sulfonate.

4. The dental gypsum-bonded investment material powder of claim 3, wherein the alkyl benzene sulfonate is a sodium dodecyl benzene sulfonate.

5. The dental gypsum-bonded investment material powder of claim 1, wherein the anionic surfactant comprises an alkyl sulfate.

6. The dental gypsum-bonded investment material powder of claim 5, wherein the alkyl sulfate comprises at least one of a sodium lauryl sulfate, a potassium lauryl sulfate, a sodium myristyl sulfate, a sodium cetyl sulfate, and a sodium stearate.

7. The dental gypsum-bonded investment material powder of claim 1, wherein the cyclic siloxane comprises 3 to 5 SiO(CH$_3$)$_2$ units.

8. The dental gypsum-bonded investment material powder of claim 1, wherein the cyclic siloxane comprises 4 SiO(CH$_3$)$_2$ units.

* * * * *